(12) United States Patent
Camporese et al.

(10) Patent No.: US 8,871,524 B2
(45) Date of Patent: Oct. 28, 2014

(54) METHODS OF PERFORMING A SIZING ANALYSIS USING A CORRECTED SIZING LADDER

(75) Inventors: Dan Camporese, New Westminster (CA); Advit Bhatt, Union City, CA (US); Josh Molho, Oakland, CA (US); Hui Xu, Palo Alto, CA (US); Ken Summers, Livermore, CA (US)

(73) Assignee: Caliper Life Sciences, Inc., Hopkinton, MA (US)

( * ) Notice: Subject to any disclaimer, the term of this patent is extended or adjusted under 35 U.S.C. 154(b) by 323 days.

(21) Appl. No.: 13/287,052

(22) Filed: Nov. 1, 2011

(65) Prior Publication Data

US 2012/0053880 A1 Mar. 1, 2012

Related U.S. Application Data

(63) Continuation-in-part of application No. 12/843,557, filed on Jul. 26, 2010, now Pat. No. 8,202,486.

(60) Provisional application No. 61/233,392, filed on Aug. 12, 2009, provisional application No. 61/266,030, filed on Dec. 2, 2009, provisional application No. 61/409,772, filed on Nov. 3, 2010.

(51) Int. Cl.
*G01N 15/06* (2006.01)
*G01N 33/00* (2006.01)
*G01N 33/48* (2006.01)
*B01L 3/00* (2006.01)
*G01N 27/447* (2006.01)

(52) U.S. Cl.
CPC ..... *B01L 3/502738* (2013.01); *G01N 27/44717* (2013.01); *B01L 2400/0655* (2013.01); *B01L 2400/0421* (2013.01); *G01N 27/44791* (2013.01); *B01L 3/502753* (2013.01); *B01L 2300/021* (2013.01); *B01L 2200/0636* (2013.01)
USPC ............ 436/161; 422/50; 422/82; 422/255; 422/549; 435/286.2; 435/287.1; 204/450; 204/600

(58) Field of Classification Search
CPC ........ G01N 15/06; G01N 33/00; G01N 33/48
USPC ........ 422/50, 82, 255, 549; 435/286.2, 287.1; 436/161; 204/450, 600
See application file for complete search history.

(56) References Cited

U.S. PATENT DOCUMENTS

| | | | |
|---|---|---|---|
| 6,221,603 B1 | 4/2001 | Mahtani | |
| 7,419,784 B2 | 9/2008 | Dubrow et al. | |
| 2002/0009721 A1* | 1/2002 | Ruiz-Martinez et al. | 435/6 |
| 2003/0032042 A1* | 2/2003 | Hunkapiller et al. | 435/6 |
| 2007/0245184 A1 | 10/2007 | Benfield et al. | |
| 2009/0149640 A1 | 6/2009 | Hu et al. | |
| 2010/0206730 A1* | 8/2010 | Hunkapiller et al. | 204/450 |

* cited by examiner

*Primary Examiner* — Brian J Sines
(74) *Attorney, Agent, or Firm* — Cardinal Law Group

(57) ABSTRACT

The invention provides methods of performing a sizing analysis. In the methods, a sizing ladder used in performing the sizing analysis is corrected. In one method, the sizing ladder is corrected for batch-to-batch variations in a sieving gel. In another method, the sizing ladder is corrected for a sample concentration that is different from the archival sizing ladder concentration. Methods are also provided in which the sizing ladder is corrected using a standard marker in a sample and/or using a real-time standard sizing ladder. The methods may be used individually or in combination.

10 Claims, 6 Drawing Sheets

METHODS OF PERFORMING A SIZING ANALYSIS USING A CORRECTED SIZING LADDER

CROSS-REFERENCE TO RELATED APPLICATIONS

This application is a continuation-in-part of Ser. No. 12/843,557 filed Jul. 26, 2010, and claims the benefit of U.S. Provisional Application No. 61/233,392 filed Aug. 12, 2009, U.S. Provisional Application No. 61/266,030 filed Dec. 2, 2009, and U.S. Provisional Application No. 61/409,772 filed Nov. 3, 2010, the disclosures of which are herein incorporated by reference.

TECHNICAL FIELD

The present disclosure is in the field of devices and systems for separation and isolation of sample components and methods for their use. In particular, described herein are methods of performing a sizing analysis using a corrected sizing ladder.

BACKGROUND OF THE INVENTION

Separations-based analyses are a prominent part of biological research, allowing one to characterize different biological samples, reaction products and the like. Examples of some of the more prevalent separations-based analyses include electrophoretic separations of macromolecular species, e.g., proteins and nucleic acids. Electrophoresis, e.g., capillary electrophoresis, has been established as a highly effective method for separating macromolecular species in order that they might be further characterized. Protein and nucleic acid molecules are two major examples of molecular species that are routinely fractionated and characterized using electrophoretic systems.

Both microfluidic and macrofluidic devices have been applied in separations-based analyses. Examples of novel microfluidic devices and methods for use in the separation of molecular, and particularly macromolecular species by electrophoretic means are described in U.S. Pat. Nos. 5,958,694, 6,032,710, and 7,419,784, for example, the entire contents of which are incorporated by reference herein. In such devices, the sample containing the macromolecular species for which separation is desired is placed in one end of a separation channel located in a microfluidic substrate and a voltage gradient is applied along the length of the channel. As the sample components (also referred to as "fragments") are electrophoretically transported along the length of the channel and through the separation (sieving) matrix disposed therein, those components are resolved. The separated components are then detected at a detection point along the length of the channel, typically near the terminus of the separation channel downstream from the point at which the sample was introduced. Following detection, the separated components are typically directed to a collection reservoir/well in the device (or to an external device such as a multiwell plate via a capillary pipettor, for example) for subsequent extraction or disposal.

In many situations, it is desirable to extract selected fragments of interest, such as DNA fragments, following the separation of the fragments into bands in the separation matrix for further processing or analysis, e.g., restriction enzyme modification, T4 ligation, PCR amplification, mass spectroscopy, or polynucleotide kinase reactions. The typical process used by laboratory researchers for extracting and isolating selected DNA fragments of interest (and other desired nucleic acid and protein fragments) from a separation matrix (such as an agarose gel) involves excising the desired fragments from the separation matrix and then extracting and purifying the excised fragment(s). First, the separated fragments are stained and illuminated by shining ultraviolet (UV) light on the fragments to visualize the separated bands. A razor blade is then used to manually cut above and below each fragment of interest so that one or more slices of the sieving can be removed. Then the DNA is extracted from the removed slices using various solutions and heating to dissolve the sieving matrix. The DNA can be further purified by standard solid phase extraction (binding the DNA to a solid surface such as glass followed by washing and finally elution). The recovered DNA can then be used for further processing or analysis. This extraction process, however, is time consuming, laborious and potentially damaging to the DNA (e.g., nicking of the DNA can occur if the DNA is exposed to ultraviolet light too long while the fragments of interest are being illuminated for excision).

Thus, in performing separations-based analyses, it would be desirable to be able to also isolate or extract one or more of the separated components in the device itself for further analysis or processing. The recovered or isolated fragments could then be used for a variety of different processes including, for example, the following: amplification using polymerase chain reaction (PCR); ligation reactions for cloning small to medium-sized strands of DNA into bacterial plasmids, bacteriophages, and small animal viruses to allow the production of pure DNA in sufficient quantities to allow its chemical analysis; adapter ligation used in high-throughput sequencing; reactions to dissolve a separated protein or nucleic acid component in a suitable matrix for further analysis by a mass spectrometer using, for example, Matrix-Assisted Laser Desorption Ionization (MALDI); binding reactions to bind a labeling agent to one or more separated protein or nucleic acid components for further analysis; or other similar post-detection processes. In addition, in the case of PCR samples, it is important to be able to separate smaller dimer and primer molecules from the main nucleic acid fragments in the sample and then isolate and collect the main nucleic acid fragments for further analysis or processing, while directing the smaller primer and dimer components to a waste reservoir/cell for removal and subsequent disposal.

A standard reference of known size is obtained by separating a standard DNA sizing ladder, e.g., for DNA separations, or a standard polypeptide of known molecular weight, e.g., for protein separations. Such a sizing ladder allows the size of unknown fragments to be determined. In a typical separation assay without fractionation (i.e., without isolation of components), the step of separating a standard sizing ladder is performed prior to transporting the first sample material through the separation channel to separate the sample material into a plurality of sample components. Thus, the entire ladder and all separated sample components have passed the detector before any sizing analysis is performed. (A ladder obtained from previous experiments is often stored and may be termed an archival ladder.) Alternatively, a ladder may be run in parallel with a sample (and may be termed a real-time ladder). In either case, the entire ladder and all separated sample components have passed a detector before any sizing analysis is performed.

To permit fractionation, a sizing analysis may need to be performed prior to the sample component(s) of interest passing the detector, thereby allowing a selected one or more separated components of interest to be diverted from the separation channel to a sample component collection location based on the determined size of the selected one or more sample components. I.e., a fractionation device may need to perform real-time sizing in order to determine the precise time to divert the material of interest to the sample component collection location. Thus, to improve sizing determinations in a fractionation device, it would be advantageous to provide methods of performing a sizing analysis using a corrected sizing ladder.

SUMMARY OF THE INVENTION

One aspect of the present invention is a method of performing a sizing analysis. An archival sizing ladder is provided, the archival sizing ladder including archival ladder migration times. Migration times are measured for a standard sizing ladder through a separation channel in a first fractionation device, the separation channel having a quantity of a first batch of sieving gel disposed therein, thereby providing a first sieving gel sizing ladder including first sieving gel sizing ladder migration times. A ratio of the first sieving gel sizing ladder migration times to the archival ladder migration times is determined, thereby providing a first correction. The first correction is encoded into a first information storage means. The first information storage means is attached to a second fractionation device, a separation channel of the second fractionation device having a quantity of the first batch of sieving gel disposed therein. The first correction encoded into the information storage means is read and applied to each archival ladder migration time, thereby providing a first corrected archival sizing ladder. A sizing analysis of the separated components of a sample disposed in the second fractionation device is then performed using the first corrected archival sizing ladder.

In another method of performing a sizing analysis, an archival sizing ladder is provided, the archival sizing ladder including archival ladder migration times. A separation channel of a fractionation device is loaded with a sample containing a low standard marker. The sample is separated into a plurality of separated components. The low standard marker is detected, thereby providing a low standard marker migration time. The low standard marker migration time is aligned with the corresponding archival sizing ladder migration time, thereby providing a corrected archival sizing ladder. A sizing analysis of the separated components is then performed using the corrected archival sizing ladder.

In yet another method of performing a sizing analysis, (a) an archival sizing ladder is provided, the archival sizing ladder including a plurality of archival ladder migration times. (b) A first channel of a fractionation device is loaded with a standard sizing ladder. (c) A second channel of the fractionation device is loaded with a sample. (d) The sample is separated into a plurality of separated components. (e) The standard sizing ladder is separated in parallel with the sample to yield a real-time ladder, the real-time ladder including a plurality of real-time ladder peaks. (f) A correction factor (CF) is calculated using the formula $CF=(t_{rt,i}-t_{rt,i-1})/(t_{a,i}-t_{a,i-1})$, where $t_{rt,i}$ is the time at which the most recent real-time ladder peak was detected, $t_{rt,i-1}$ is the time at which the previous real-time ladder peak was detected, and $(t_{a,i}-t_{a,i-1})$ is the migration time difference between the archival ladder peak corresponding to real-time ladder peak (i) and the archival ladder peak corresponding to real-time ladder peak (i−1). (g) The correction factor is applied to each archival ladder migration time corresponding to a not-yet-detected real-time ladder peak, thereby providing one or more corrected archival ladder migration times. (h) A sizing analysis of the separated components is performed using a corrected archival sizing ladder consisting of detected real-time ladder peak migration times and corrected archival ladder migration times. (i) Steps (f) through (g) are repeated for each of the plurality of real-time ladder peaks.

In still another method of performing a sizing analysis, the following steps are performed. (a) A sizing ladder is provided. (b) A concentration is provided for each peak in the sizing ladder. (c) A sample is separated into a plurality of components in a fractionation device. (d) The sample concentration up to the migration time $(t_i)$ of each ladder peak (i) is computed. (e) The sample concentration up to the migration time $(t_i)$ is normalized to the concentration in the sizing ladder up to the migration time $(t_i)$ using the formula $C_N(i)=C_S(t_i)/C_L(i)$, where $C_S(t_i)$ is the cumulative sample concentration up to the time $t_i$, and $C_L(i)$ is the sum of the ladder peak concentrations up to the $i^{th}$ ladder peak. (f) The sizing ladder peak (i) migration time is corrected using the formula $t^*_i=f(t_i,C_N,p_1, p_2 p_3, \ldots p_n)$, where f is a function of $t_i$, $C_N$, and any number of specified parameters $(p_n)$. (g) Steps (c) through (f) are repeated for each component of the plurality of components; and (h) a sizing analysis of the separated sample is performed using the corrected ladder peak migration times.

The aforementioned and other features and advantages of the invention will become further apparent from the following detailed description of the presently preferred embodiments, read in conjunction with the accompanying drawings, which are not to scale. In the drawings, like reference numbers indicate identical or functionally similar elements. The detailed description and drawings are merely illustrative of the invention, rather than limiting, the scope of the invention being defined by the appended claims and equivalents thereof.

DETAILED DESCRIPTION OF THE PRESENTLY PREFERRED EMBODIMENTS

Figure 1:
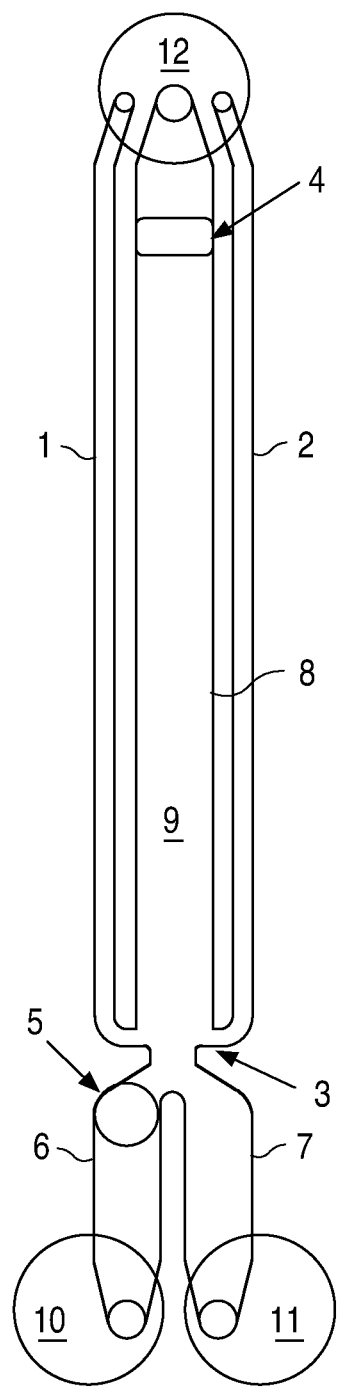
FIG. 1 is a schematic illustration of a device for isolating one or more sample components of a sample material following separation of the sample material into a plurality of sample components
Figure 2:
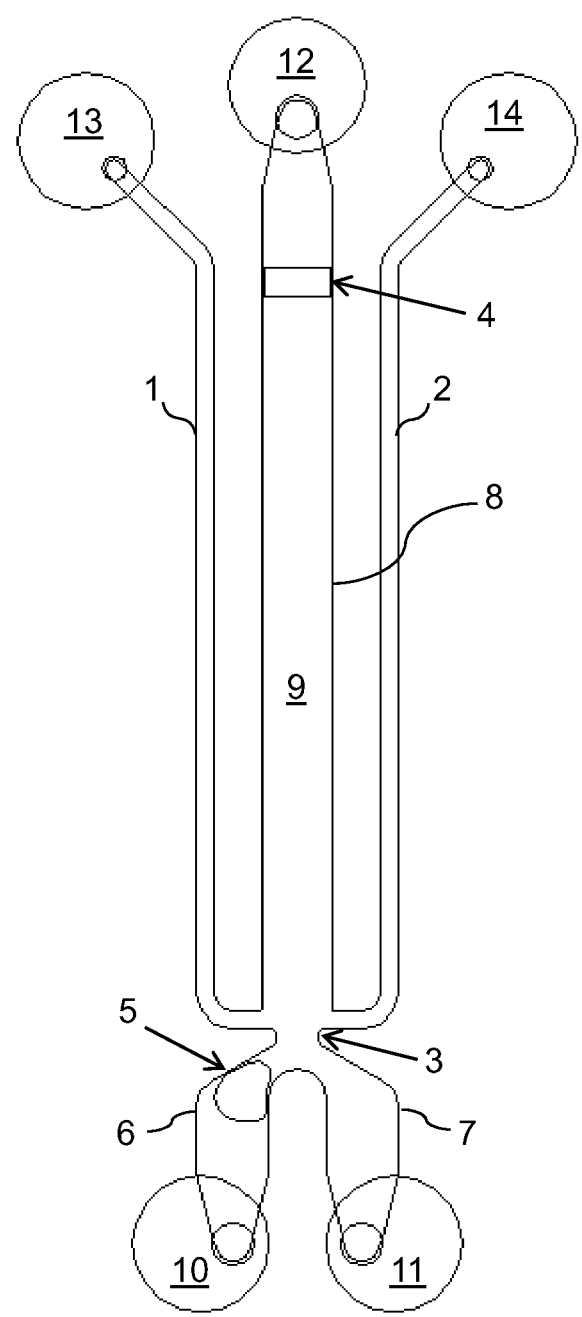
FIG. 2 is a schematic illustration of another device for isolating one or more sample components of a sample material following separation of the sample material into a plurality of sample components.

FIGS. 1 and 2 illustrate devices for isolating one or more sample components of a sample material following separation of the sample material into a plurality of sample components. The devices comprise first and second pinching channels 1 and 2, a switching region 3, a loading well 4, a collection well 5, a collection leg 6, a waste leg 7, a separation channel 8, a sieving matrix 9, and reservoirs 10-12. Reservoirs 10 and 11 are waste reservoirs. The device of FIG. 1 comprises a single buffer reservoir 12, while the device of FIG. 2 comprises three buffer reservoirs, reservoirs 12, 13, and 14. The illustrated devices are described in detail in co-pending U.S. patent application Ser. No. 12/843,557.

In operation, a sample is deposited into loading well 4. A voltage is applied to buffer reservoir 12, and a different voltage is applied to waste reservoir 11 to electrophoretically separate the sample into a plurality of sample components in separation channel 8. Initially, no electrical connection is made to waste reservoir 10 in order to maintain zero current within collection leg 6, thereby directing the separated sample into waste leg 7 and waste reservoir 11 until a component of the sample desired for isolation and collection reaches switching region 3. Alternatively, the fluid direction system may control the voltage at waste reservoir 10 in order to maintain zero current. Note that the term "zero current" denotes a current that is negligible as compared to the current in the other leg, such as a current that is less than 2% of the current in the other leg.

Once the one or more components that are to be isolated and collected are within switching region 3, a voltage is applied to waste reservoir 10, and a zero current is maintained at waste reservoir 11. This switches the direction of the sample stream from waste leg 7 into collection leg 6. The redirection of the sample stream is timed to isolate only the desired component(s) of the sample. Once the one or more desired components are within collection leg 6 and positioned at the location of collection well 5, the sample stream is directed back into waste leg 7 and waste reservoir 11 by once again controlling zero current to waste reservoir 10 and resuming the original voltage to waste reservoir 11. Once zero current is imposed at the electrical connection to waste reservoir 10, transport into collection leg 6 stops, and the desired one or more components of the sample remain in place within collection leg 6 at the location of collection well 5. The sample component(s) may then be removed from collection well 5 manually using, for example, a pipettor, or may be withdrawn by an automated sample transfer device.

The present invention provides methods of performing a sizing analysis using a corrected archival or real-time sizing ladder, thereby improving the accuracy and precision of isolating sample component(s) of interest (i.e., of fractionation of fragmented samples) using the above-described device or another.

For fractionation to take place, sizing of the components (also referred to as "fragments") in a stream of separated sample components may need to be done in real time to allow diversion of only the desired components to a collection location. To achieve fractionation using devices such as those illustrated in FIGS. 1 and 2, or other fractionation devices known in the art, times must be determined at which a switching voltage is to be applied and subsequently removed from the device to divert the flow into the collection leg for only the desired size range. This determination is performed by establishing a relationship between migration time and size and using this determination to calculate the time in the future when the switch is to be applied and then removed.

Sizing may be accomplished using an archival sizing ladder that provides a table of values relating fragment size to migration time of the fragment through a separation channel. An archival ladder is obtained by separating and detecting a standard DNA sizing ladder (a solution of DNA molecules of different lengths) for DNA separations, for example, or a standard polypeptide of known molecular weight (for protein separations) under known conditions in a device having the same configuration as the device that will be used to separate and fractionate a sample. (Note that as used herein the term "ladder" may denote either the material that is separated and detected or migration times of separated components of the material, the separated components being typically identified as peaks in an electropherogram. The intended meaning will be specified or will be clear from the term read in context.)

Because an archival ladder is obtained by experiment, it is completely accurate only for the specific separation conditions used for the experiment. These conditions may vary. Therefore, an archival ladder is preferably corrected before sizing is carried out based on the actual separation conditions experienced by a sample during a run. Note that in any of the methods described below, the archival ladder may be permanently stored in the memory of an instrument configured to receive the device. Alternatively, ladder information may be provided encoded in an information storage means attached to or otherwise provided with the device (e.g., on a card) and read by the instrument. This ladder information then becomes the archival ladder used in performing one or more sizing analyses on the device. The ladder information may be encoded on the same information storage means used to provide corrections for the archival ladder or on a separate archival ladder information storage means. The below methods may be carried out independently of one another or may be used in any combination, including a combination that includes all of the methods. The corrected sizing ladder obtained from one method may then become the archival or stored ladder for a subsequently performed method.

Correction of an Archival Ladder for Batch-to-Batch Variations in a Sieving Gel

While geometric and electrical conditions can be replicated easily from one device to another, it is more difficult to replicate the exact sieving properties of the gel used when running the archival ladder that is stored in the instrument. To compensate for batch-to-batch variations in the sieving gel, migration times may be measured for the standard sizing ladder in each gel batch used to fill a device, and the ratio of these migration times to the archival ladder migration times for that batch may be determined, thereby providing a correction for each migration time in the archival ladder table.

This ratio may be coded into an information storage means such as, for example, a barcode that is attached to each device or printed on a card provided with each device, with the ratio being read into the instrument at the time the device is loaded onto the instrument. The ratio is applied to the migration times of the archival ladder just before a sample is run, and these corrected times are used in sizing of sample fragments, where the sizing may be used to determine diversion times for diversion of fragments of interest into a collection location. A correction value may range from, for example, −30% to +30% of the migration time contained in the archival sizing ladder.

Figure 3:
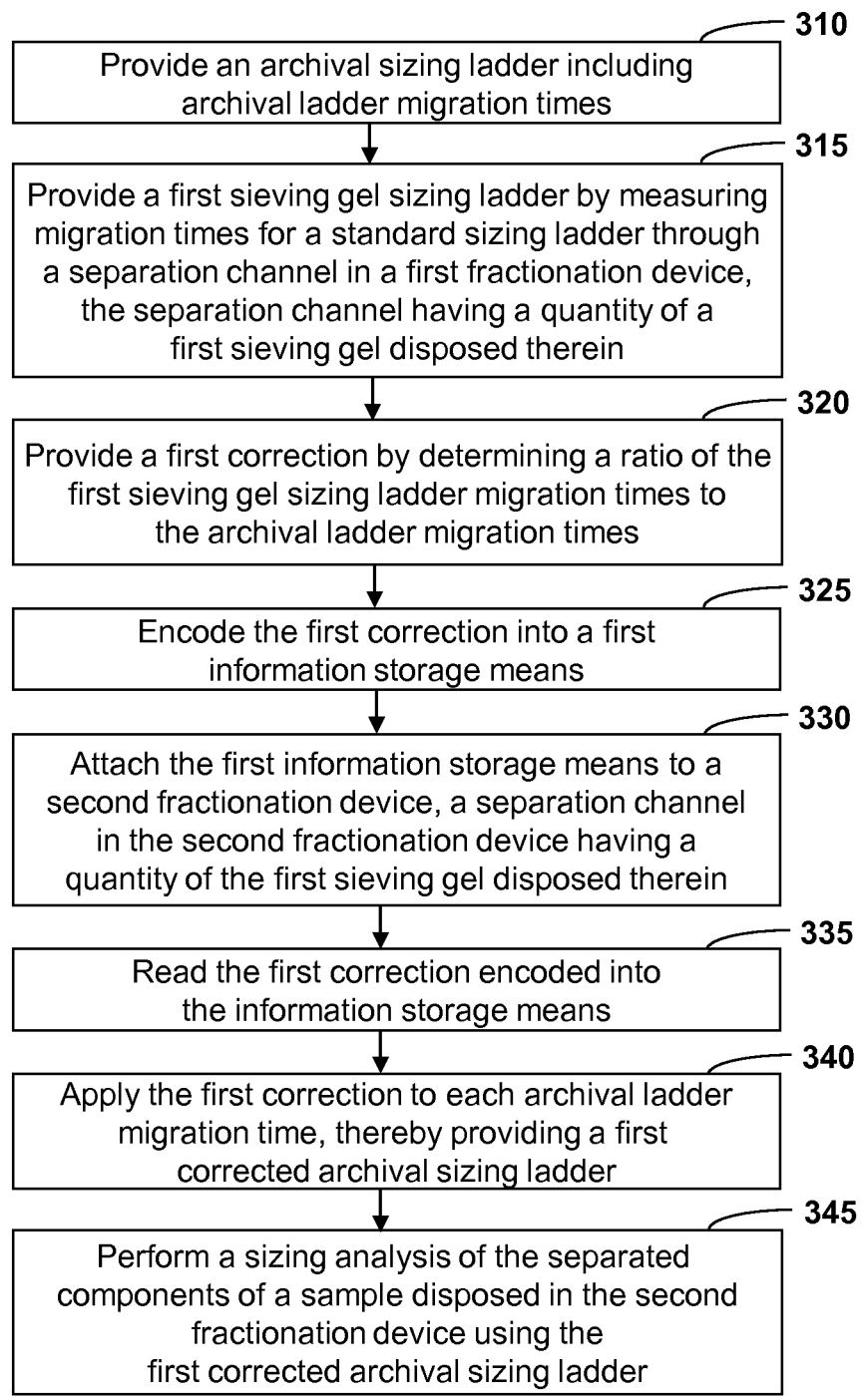
FIG. 3 is a flow diagram of one method of performing a sizing analysis, in accordance with the present invention, the method correcting for batch-to-batch variations in a sieving gel.

FIG. 3 shows a flow diagram of a method of performing a sizing analysis in accordance with the present invention. An archival sizing ladder is provided, the archival sizing ladder including archival ladder migration times (Block 310). Migration times are measured for a standard sizing ladder through a separation channel in a first fractionation device, the separation channel having a quantity of a first batch of sieving gel disposed therein, thereby providing a first sieving gel sizing ladder including first sieving gel ladder migration times (Block 315). A ratio of the first sieving gel sizing ladder migration times to the archival ladder migration times is determined, thereby providing a first correction (Block 320).

The first correction is encoded into a first information storage means (Block 325). The first information storage means is attached to a second fractionation device (Block 330), a separation channel of the second fractionation device having a quantity of the first batch of sieving gel disposed therein. The first correction encoded into the information storage means is read (Block 335) and applied to each archival ladder migration time, thereby providing a first corrected archival sizing ladder (Block 340). A sizing analysis of the separated components of a sample disposed in the second fractionation device is performed using the first corrected archival sizing ladder (Block 345). One or more of the separated components may be directed into a collection well.

The above method may further comprise the following steps. Migration times for the standard sizing ladder through a separation channel in a third fractionation device are measured, the separation channel having a quantity of a second batch of sieving gel disposed therein, thereby providing a second sieving gel sizing ladder. A ratio of the second sieving gel sizing ladder migration times to the archival ladder migration times is determined, thereby providing a second correction. The second correction is encoded into a second information storage means. The information storage means is attached to a fourth fractionation device, a separation channel of the fourth fractionation device having a quantity of the second batch of sieving gel disposed therein. The second correction encoded into the information storage means is read and applied to each archival ladder migration time, thereby providing a second corrected archival sizing ladder. A sizing analysis of the separated components of a sample disposed in the fourth fractionation device is then performed using the second corrected archival sizing ladder.

Example 1

In the present example, a device includes a 2D matrix barcode label that contains the following information.
Version
Assay
Manufacturing Date
Expiration Date
Repetition Number
Serialization Number
Ladder Correction Data The barcode consists of a maximum of 26 characters, with each character comprising one of 64 printable ASCII characters. The ASCII characters used are the 62 alphanumeric characters plus the characters ? and @. This allows for a maximum $64^{26}$ different codes.

The characters read out of the barcode are converted by the barcode reader into the corresponding numeric value, and those values are used by the software for input based on the character position.

Of particular interest for the present invention, each ladder peak has a number representing the % change in migration time compared to the archival ladder. Not all characters need to be used, but potentially up to 16 different peaks are available. The range of data is from −30% to +30%, in increments of 1%, and is mapped to the barcode character set as follows:

Character '0' = decimal 0 = null (no data)
Character '1' = decimal 1 = −30%
Character '2' = −29%
...
Character 'w" = decimal 60 = +29%
Character 'x' = decimal 61 = +30%

Correction of an Archival Ladder Using a Low Standard Marker in a Sample

Samples being electrophoretically separated are commonly run with one or more standard reference materials, also called standard markers, that are used to characterize the sample constituents. In the present embodiment, a low standard marker contained in a sample is used in combination with an archival ladder to correct the archival ladder, thereby improving real-time sizing of fragments. As used herein, a "low standard marker" is a marker that matches the first peak of the ladder being used to perform a sizing analysis. The present method may be used in combination with the batch-to-batch sieving gel correction method described above, with the sieving gel correction method carried out at the start of the run to provide an archival ladder for use in the present method.

Where a low standard marker is contained in the sample, the archival ladder and standard and sample markers are aligned during the run, resulting in an adjustment of the sample migration times relative to the ladder. Diversion times are corrected using the aligned sample migration times once the low standard marker in the sample has passed the detector. Running the low standard marker provides a known point for correcting the archival sizing ladder.

Figure 4:
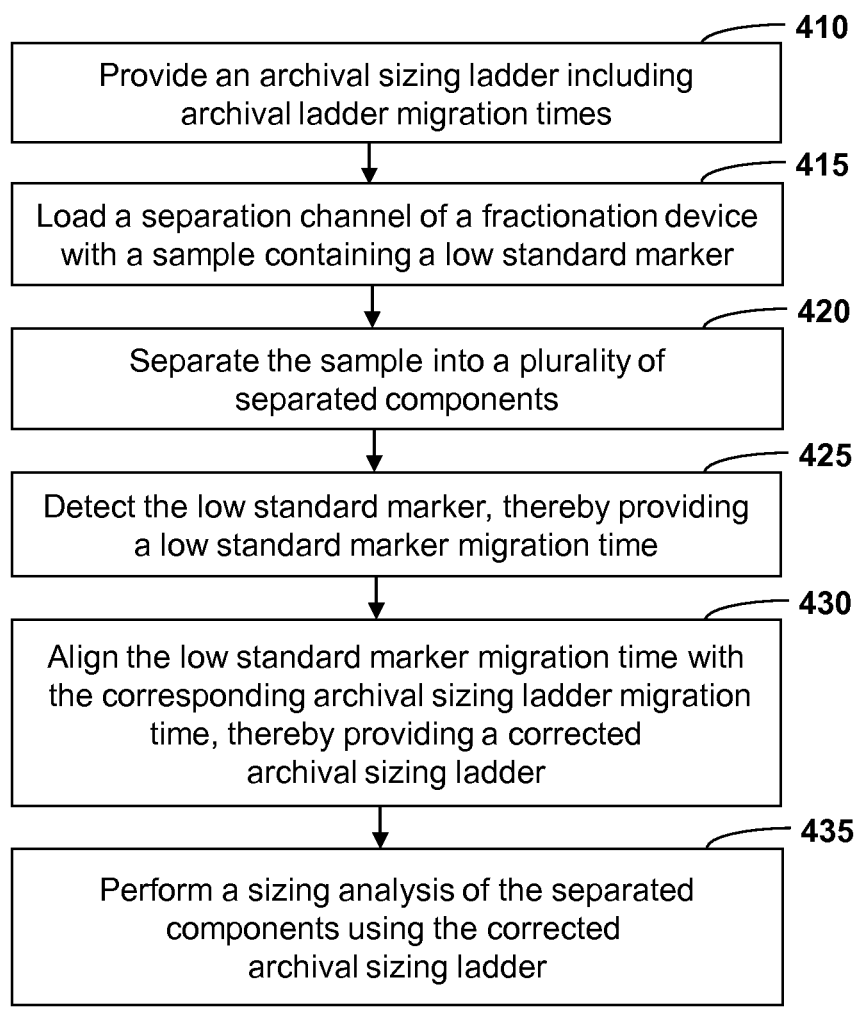
FIG. 4 is a flow diagram of another method of performing a sizing analysis, in accordance with the present invention, the method correcting an archival sizing ladder using a low standard marker in a sample.

FIG. 4 shows a flow diagram of a method of performing a sizing analysis in accordance with the present invention. An archival sizing ladder is provided, the archival sizing ladder including archival ladder migration times (Block 410). A separation channel of a fractionation device is loaded with a sample containing a low standard marker (Block 415). The sample is separated into a plurality of separated components (Block 420). The low standard marker is detected, thereby providing a low standard marker migration time (Block 425). The low standard marker migration time is aligned with the corresponding archival sizing ladder migration time, thereby providing a corrected archival sizing ladder (Block 430). A sizing analysis of the separated components is then performed using the corrected archival sizing ladder (Block 435). One or more of the separated components may be directed into a collection well. Note that in this context, alignment of the low standard marker migration time with the corresponding archival sizing ladder migration time to provide a corrected archival sizing ladder means that the archival ladder migration times (including the low marker) are multiplied by the ratio $(t_{s,lm}/t_{a,lm})$, where $t_{s,lm}$ and $t_{a,lm}$ are the sample and archival low marker times, respectively. Such an alignment corrects for possible differences between electric fields used in generating the archival ladder data and electric fields used in separating the sample.

Correction of an Archival Ladder Using a Real-Time Standard Sizing Ladder

Information obtained from a real-time ladder, i.e., a standard sizing ladder running alongside (e.g., in parallel with) the sample, may be used in combination with the archival ladder to provide improved sizing of separated sample components. Because the archival ladder may not have been run under the exact same conditions as those being experienced by the real-time ladder and the sample, migration times between peaks on the archival ladder and migration times between corresponding peaks on the real-time ladder may differ. For example, 240 seconds may separate the 300 BP peak and the 200 BP peak in the archival ladder, while 216 seconds may separate the 300 BP peak and the 200 BP peak in the real-time ladder. Such differences in migration times between the archival ladder and the real-time ladder can be used to correct (i.e., update) the archival ladder, allowing for better sizing of sample components.

A correction factor (CF) is determined using the following formula:

$$CF = (t_{rt,i} - t_{rt,i-1})(t_{a,i} - t_{a,i-1})$$

where $t_{rt,i}$ is the time at which the most recent real-time ladder peak was detected,
$t_{rt,i-1}$ is the time at which the previous real-time ladder peak was detected; and
$(t_{a,i} - t_{a,i-1})$ is the migration time difference between the archival ladder peak corresponding to real-time ladder peak (i) and the archival ladder peak corresponding to real-time ladder peak (i−1).

Thus, in the example given above, where 240 seconds separate the 300 BP peak and the 200 BP peak in the archival ladder, and 216 seconds separate the 300 BP peak and the 200 BP peak in the real-time ladder, the correction factor (CF) would be 90%.

The correction factor is then applied to migration times in the archival ladder that correspond to peaks not yet seen in the real-time (standard sizing) ladder to provide corrected archival ladder migration times as demonstrated below:

$$t^*_{a,i+1} = t_{rt,i} + (t_{a,i+1} - t_{a,i}) \times CF$$

$$t^*_{a,i+2} = t^*_{a,i+1} + (t_{a,i+2} - t_{a,i+1}) \times CF$$

$$t^*_{a,i+3} = t^*_{a,i+2} + (t_{a,i+3} - t_{a,i+2}) \times CF$$

etc.

As each new real-time ladder peak is detected, the process above is repeated, i.e., a new correction factor is determined, and the new correction factor is applied to migration times in the original archival ladder that correspond to peaks not yet detected in the real-time ladder to produce corrected archival ladder migration times. These corrected archival ladder migration times are, in effect, predicted migration times for anticipated real-time ladder peaks. Thus, each corrected archival sizing ladder includes actual migration times for the detected real-time ladder peaks and predicted migration times for the anticipated real-time ladder peaks. Sizing of separated sample components is performed using the most recently corrected archival ladder.

Figure 5:
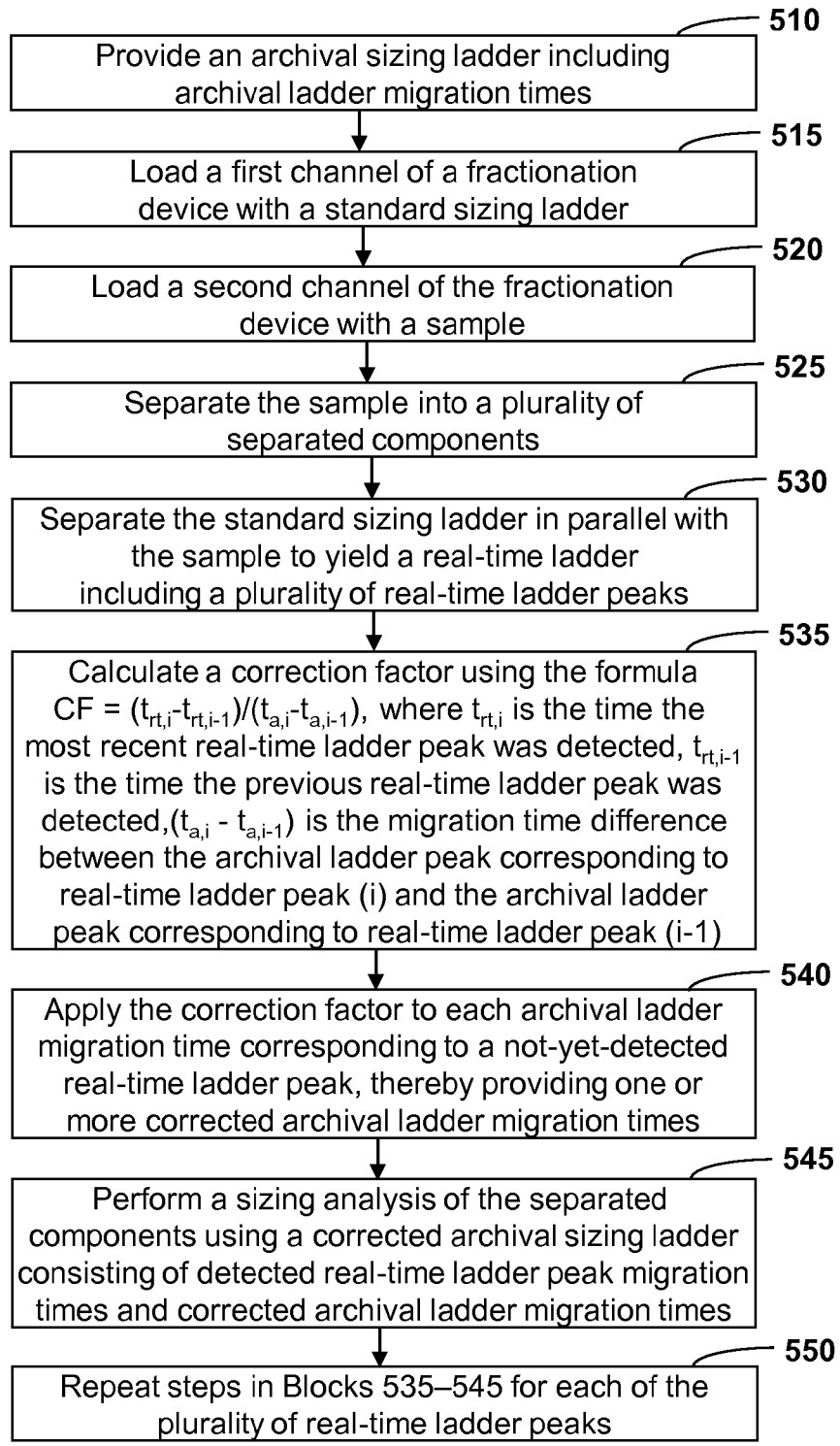
FIG. 5 is a flow diagram of yet another method of performing a sizing analysis, in accordance with the present invention, the method correcting an archival sizing ladder using a real-time standard sizing ladder.

FIG. 5 shows a flow diagram of a method of performing a sizing analysis in accordance with the present invention. An archival sizing ladder is provided, the archival sizing ladder including a plurality of archival ladder migration times (Block 510). A first channel of a fractionation device is loaded with a standard sizing ladder (Block 515). A second channel of the fractionation device is loaded with a sample (Block 520). The sample is separated into a plurality of separated components (Block 525). The standard sizing ladder is separated in parallel with the sample to yield a real-time ladder, the real-time ladder including a plurality of real-time ladder peaks (Block 530). A correction factor (CF) is calculated using the formula $CF = (t_{rt,i} - t_{rt,i-1})/(t_{a,i} - t_{a,i-1})$, where $t_{rt,i}$ is the time at which the most recent real-time ladder peak was detected, is the time at which the previous real-time ladder peak was detected, and $(t_{a,i} - t_{a,i-1})$ is the migration time difference between the archival ladder peak corresponding to real-time ladder peak (i) and the archival ladder peak corresponding to real-time ladder peak (i−1) (Block 535). The correction factor is applied to each archival ladder migration time corresponding to a not-yet-detected real-time ladder peak, thereby providing one or more corrected archival ladder migration times (Block 540). A sizing analysis of the separated components is performed using a corrected archival sizing ladder consisting of detected real-time ladder peak migration times and corrected archival ladder migration times (Block 545). Steps in Blocks 535 through 545 are repeated for each of the plurality of real-time ladder peaks (Block 550). One or more of the separated components may be directed into a collection well. In alternative embodiments, the steps in Blocks 535 through 545 may be repeated only until immediately before, immediately after, or the time when the separated components are directed into the collection well.

Correction of an Archival Ladder for Sample Concentration

The size of a sample fragment in a separation channel is typically determined by comparison to the migration times of standard sizing ladder fragments of known size, the sizing being based on the assumption that sample fragments of the same size as ladder fragments move through a gel at the same speed. This assumption may not be valid when the concentration of material in the sample is different than that in the standard sizing ladder. When the sample concentration exceeds that of the standard sizing ladder, sample fragments move at different speeds than equal size fragments in the standard sizing ladder. This migration change may occur, for example, because when the sample material is of high concentration, it depletes a charged dye that flows in the opposite direction and, as a result, upstream fragments move through the gel more quickly than did same-sized fragments in the standard sizing ladder.

Compensation for this acceleration in the sample may be performed by applying a concentration relative correction to the standard sizing ladder fragment migration time before using the standard sizing ladder to compute fragment size in the sample. For example, the correction may be proportional to the ratio of ladder concentration to sample concentration up to the point in time a particular ladder fragment is detected. An empirically determined acceleration factor multiplied by the concentration ratio provides the fractional amount the standard sizing ladder fragment migration time is to be reduced. Note that for the present method, the standard sizing ladder may be either an archival ladder or a real-time ladder running alongside the sample being separated.

Figure 6:
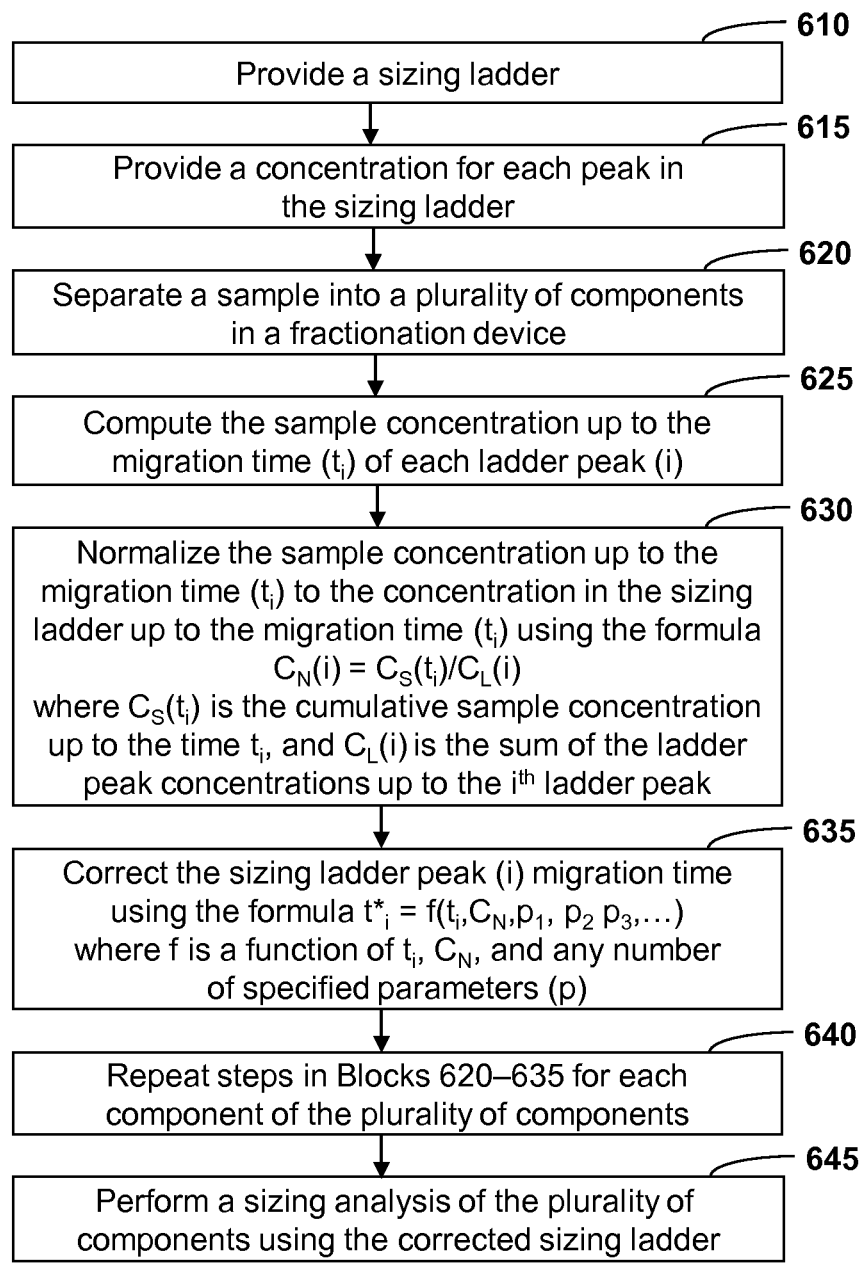
FIG. 6 is a flow diagram of still another method of performing a sizing analysis, the method correcting for a sample concentration that is different from an archival or real-time sizing ladder concentration.

FIG. 6 shows a flow diagram of a method of performing a sizing analysis in accordance with the present invention. A sizing ladder is provided (Block 610). A concentration is provided for each peak in the sizing ladder (Block 615). A sample is separated into a plurality of components in a fractionation device (Block 620). The sample concentration up to the migration time $(t_i)$ of each ladder peak (i) is computed. (Block 625). The sample concentration up to the migration time $(t_i)$ is normalized $(C_N)$ to the concentration in the sizing ladder up to the migration time $(t_i)$ using the formula $C_N(i) = C_S(t_i)/C_L(i)$, where $C_S(t_i)$ is the cumulative sample concentration up to the time $t_i$, and $C_L(i)$ is the sum of the ladder peak concentrations up to the $i^{th}$ ladder peak (Block 630). The sizing ladder peak (i) migration time is corrected using the formula $t^*_i = f(t_i, C_N, p_1, p_2 p_3, \ldots p_n)$, where f is a function of $t_i$, $C_N$, and any number of specified parameters $(p_n)$ (Block 635). Steps in Blocks 620-635 are repeated for each component of the plurality of components (Block 640). A sizing analysis of the detected component is performed using the corrected sizing ladder (Block 645). The exact form of the formula used in the step of Block 635 may be $t^*_i = t_i * [1 - C_N(i) * LTA]$, where $t^*_i$ is the corrected migration time of the $i^{th}$ ladder peak, and LTA is the ladder time advance factor, as shown in the following example.

Example 2

To account for the effect of sample concentration on fragment mobility, the ladder times are accelerated when the sample concentration is higher than that of the ladder. The effect is small and difficult to model accurately so a simple linear correction is used. For each ladder peak, the sample concentration is computed up to the migration time of that peak. This concentration is normalized ($C_N$) to the total concentration in the ladder.

$$C_N(i)=C_S(t_i)/C_L(i)$$

where $C_S(t_i)$ is the cumulative sample concentration up to the time $t_i$, and $C_L(i)$ is the sum of the ladder peak concentrations up to the $i^{th}$ ladder peak The ladder time is corrected using the formula:

$$t^*_i=t_i*[1-C_N(i)*\text{LTA}]$$

where t*i is the corrected migration time of the ith ladder peak, and LTA is the ladder time advance factor Empirical analysis has found that a value of 0.007 provides sufficient time advance to correct the sizing in the sample at an extraction size of 500 BP for a sample concentration of 100 ng/μl compared to the 22 ng/μl found in the ladder.

This sizing correction may be computed throughout an extraction run so that the decision as to when to begin and end fractionation will include this correction. In addition, the correction may be applied only if $C_N(i)>1.0$ and will reduce the migration time by no more than 85% of each ladder migration time; i.e. $0<C_N(i)*\text{LTA}<0.1$.

While the embodiments of the invention disclosed herein are presently considered to be preferred, various changes and modifications can be made without departing from the spirit and scope of the invention. The scope of the invention is indicated in the appended claims, and all changes and modifications that come within the meaning and range of equivalents are intended to be embraced therein.

What is claimed is:

1. A method of performing a sizing analysis of separated components, the method comprising:

providing an archival sizing ladder, the archival sizing ladder including previously measured archival ladder migration times;

measuring migration times for a standard sizing ladder through a separation channel in a first fractionation device, the separation channel having a quantity of a first batch of sieving gel disposed therein, thereby providing a first sieving gel sizing ladder, the first sieving gel sizing ladder including first sieving gel ladder migration times;

determining a ratio of the first sieving gel sizing ladder migration times to the archival ladder migration times, thereby providing a first correction;

encoding the first correction into a first information storage means;

attaching the first information storage means to a second fractionation device, a separation channel of the second fractionation device having a quantity of the first batch of sieving gel disposed therein;

reading the first correction encoded into the information storage means;

applying the first correction to each archival ladder migration time, thereby providing a first corrected archival sizing ladder; and performing a sizing analysis of the separated components of a sample disposed in the second fractionation device using the first corrected archival sizing ladder in comparison with a parameter for at least one of the separated components, the parameter being selected from the group consisting of separated component migration time and separated component band position.

2. The method of claim 1 further comprising:
directing one or more of the separated components into a collection well.

3. The method of claim 1, wherein the first correction is in the range of −30% to +30% of each archival ladder migration time.

4. The method of claim 1, wherein the first information storage means is a barcode.

5. The method of claim 1, wherein the archival sizing ladder is stored within an instrument configured to receive each of the first and the second fractionation devices, and wherein the instrument reads the first correction.

6. The method of claim 1 wherein the archival sizing ladder is stored on the first information storage means.

7. The method of claim 1 wherein the archival sizing ladder is stored on an archival ladder information storage means disposed on one of the first fractionation device and the second fractionation device.

8. The method of claim 1 further comprising:

measuring migration times for the standard sizing ladder through a separation channel in a third fractionation device, the separation channel having a quantity of a second batch of sieving gel disposed therein, thereby providing a second sieving gel sizing ladder, the second sieving gel sizing ladder including second sieving gel ladder migration times;

determining a ratio of the second sieving gel sizing ladder migration times to the archival ladder migration times, thereby providing a second correction;

encoding the second correction into a second information storage means;

attaching the information storage means to a fourth fractionation device, a separation channel of the fourth edition fractionation device having a quantity of the second batch of sieving gel disposed therein;

reading the second correction encoded into the second information storage means; and applying the second correction to each archival ladder migration time, thereby providing a second corrected archival sizing ladder; and performing a sizing analysis of the separated components of a sample disposed in the fourth fractionation device using the second corrected archival sizing ladder.

9. The method of claim 8, wherein the second correction is in the range of −30% to +30% of each archival ladder migration time.

10. The method of claim 8, wherein the second information storage means is a barcode.

* * * * *